United States Patent
Lee (10) Patent No.: US 6,206,919 B1
(45) Date of Patent: Mar. 27, 2001

(54) METHOD AND APPARATUS TO CORRECT REFRACTIVE ERRORS USING ADJUSTABLE CORNEAL ARCUATE SEGMENTS

(76) Inventor: Joseph Y. Lee, 11435 Via Lido, Loma Linda, CA (US) 92354

( * ) Notice: Subject to any disclaimer, the term of this patent is extended or adjusted under 35 U.S.C. 154(b) by 0 days.

(21) Appl. No.: 09/229,488

(22) Filed: Jan. 13, 1999

Related U.S. Application Data (60) Provisional application No. 60/071,405, filed on Jan. 14, 1998.

(51) Int. Cl.[7] .................................................... A61F 2/14
(52) U.S. Cl. ..................... 623/5.12; 623/5.11; 623/4.1
(58) Field of Search ................... 623/4.1, 5.11, 623/5.12

(56) References Cited

U.S. PATENT DOCUMENTS

| | | | |
|---|---|---|---|
| 4,298,004 | 11/1981 | Schachar et al. | 128/305 |
| 4,452,235 | 6/1984 | Reynolds | 128/1 R |
| 4,607,617 | 8/1986 | Choyce | 128/1 R |
| 4,624,669 | 11/1986 | Grendahl | 623/5 |
| 4,655,774 | 4/1987 | Choyce | 623/5 |
| 4,688,570 | 8/1987 | Kramer et al. | 128/305 |
| 4,815,463 | 3/1989 | Hanna | 128/305 |
| 4,834,750 | 5/1989 | Gupta | 623/6 |
| 4,941,093 | 7/1990 | Marshall | 364/413.01 |
| 4,961,744 | 10/1990 | Kilmer et al. | 606/166 |
| 4,976,719 | 12/1990 | Siepser | 606/151 |
| 5,090,955 | 2/1992 | Simon | 604/51 |
| 5,123,921 | 6/1992 | Werblin et al. | 623/5 |
| 5,188,125 | 2/1993 | Kilmer et al. | 128/898 |
| 5,236,970 | 8/1993 | Christ et al. | 523/113 |
| 5,300,118 | 4/1994 | Silvestrini et al. | 623/5 |
| 5,312,424 | 5/1994 | Kilmer et al. | 606/151 |
| 5,318,047 | 6/1994 | Davenport et al. | 8/632 |
| 5,331,073 | 7/1994 | Weinschenk, III et al. | 526/264 |
| 5,372,580 | 12/1994 | Simon et al. | 604/22 |
| 5,391,201 | 2/1995 | Barrett et al. | 623/5 |

(List continued on next page.)

FOREIGN PATENT DOCUMENTS

| | | | |
|---|---|---|---|
| 388746 | 7/1973 | (RU) | 31/16 |

OTHER PUBLICATIONS

McCarey, B. et al., "Refractive Keratoplasty with Intrastromal Hydrogel Ienticular Implants," Assoc. For Res. In Vis. And Ophthal., Inc., vol. 21, 21, No. 1, Part 1, Jul. 1981. pp. 107–115.

Beekhuis, W.H. et al., "Hydration Stability of Intracorneal Hydrogel Implants," Investigative Ophthalmology & Visual Science, vol. 26, Nov. 1985, pp. 1634–1636.

Beekhuis, W.H. et al., "Hydrogel Keratophakia: A Microkeratome Dissection in the Monkey Model," British Journal of Ophthalmology, 1986, pp. 192–198.

McCarey, B. et al., "Refractive Keratoplasty in Monkeys Using Intracorneal Lenses of Various Refractive Indexes," Arch Ophthalmol, vol. 105, Jan. 1987, pp. 123–126.

Beekhuis, W.H. et al., "Complications of Hydrogel Intracorneal Lenses in Monkeys," Arch Ophthalmol, vol. 105, Jan. 1987, pp. 116–122.

(List continued on next page.)

Primary Examiner—Dinh X. Nguyen
(74) Attorney, Agent, or Firm—McCutchen, Doyle, Brown & Enersen, LLP (57) ABSTRACT

A method and apparatus for adjusting corneal curvature of the eye comprising an adjustable corneal arcuate segment or segments which is implantable into the cornea. The arcuate segment is a flexible hollow shell composed of a synthetic or a natural material, with an annular chamber that is filled with a predetermined amount of a biocompatible material. The corneal curvature is adjusted by removing or augmenting the predetermined amount of biocompatible material contained in the arcuate segment.

22 Claims, 11 Drawing Sheets

U.S. PATENT DOCUMENTS

| | | | |
|---|---|---|---|
| 5,405,384 | 4/1995 | Silvestrini | 623/5 |
| 5,466,260 | 11/1995 | Silvestrini et al. | 623/5 |
| 5,480,950 | 1/1996 | Wang et al. | 526/258 |
| 5,505,722 | 4/1996 | Kilmer et al. | 606/1 |
| 5,547,468 | 8/1996 | Simon et al. | 604/21 |
| 5,607,437 | 3/1997 | Simon et al. | 606/166 |
| 5,693,092 | 12/1997 | Silvestrini et al. | 623/5 |
| 5,733,334 | 3/1998 | Lee | 623/5 |
| 5,855,604 * | 1/1999 | Lee | 623/5 |
| 5,876,439 * | 3/1999 | Lee | 623/5 |

OTHER PUBLICATIONS

Fleming, J. et al., "The Intrastromal Corneal Ring: Two Cases in Rabbits," Journal of Refractive Surgery, vol. 3, No. 6, Nov./Dec. 1987, pp. 227–232.

Climenhaga, H. et al., "Effect of Diameter and Depth on the Response to Solid Polysulfone Intracorneal Lenses in Cats," Arch Ophthalmol, vol. 106, Jun. 1988, pp. 818–824.

Burris, T. et al., "Effects of Intrastromal Corneal Ring Size and Thickness on Corneal Flattening in Human Eye," Refractive & Corneal Surgery, vol. 7, Jan./Feb. 1991, pp. 46–50.

Simon, G. et al., "Refractive Remodeling of the Cornea by Intrastromal Rings," Abstracts, Eighth International Congress of Eye Research, The International Society of Eye Research, Sep. 1988.

Burris, T. et al., "Flattening of Central Corneal Curvature with Intrastromal Corneal Rings of Increasing Thickness: An Eye–Bank Study," J Cataract Refract. Surg., vol. 19, 1993, pp. 182–187.

Elander, R. et al., "Principles and Practice of Refractive Surgery," W.B. Saunders Company, including Chap. 21, *Alloplastic Materials in Lamellar Surgery*, by McCarey, Chap. 39, *Synthetic Epikeratoplasty*, by Thompson et al., Chap 40, Intrastromal Corneal Ring, by Schanzlin et al., 1997.

Azar, D., "Refractive Surgery," Appleton & Lange, including Chap. 15, *Corneal Biomechanics in Refractive Surgery*, by Hjortdal, Chap. 27, *The Intrastromal Corneal Ring for the Correction of Myopia*, by Verity et al., Chap. 28, *Intracorneal Alloplastic Inclusions*, by Khoury et al., 1997.

Barraquer, J., "Basis of Refractive Keratoplasty," Refractive & Corneal Surgery, vol. 5, May/Jun. 1989, pp. 179–193.

Blavatskaia, E.D., "The Use of Intralamellar Homoplasty in Order to Reduce Refraction of the Eye," Arch. Soc. Ophthalmol. Optom., vol. 6, 1988.

Harr, D., "KeraVision Begins Implanting Corneal Reshaping Device in Blind Eyes," Refractive & Corneal Surgery, vol. 7, Sep./Oct. 1991, p. 343.

Simon, G. et al., "Gel Injection Adjustable Keratoplasty," Graefe's Arch Clin Exp. Ophthalmol, 1991, pp. 418–425.

Simon, G. et al., "Modification, Calibration, and Comparative Testing of an Automated Surgical Keratometer," Refractive & Corneal Surgery, vol. 7, Mar./Apr. 1991, pp. 151–160.

Thompson, K. et al., "Emerging Technologies for Refractive Surgery: Laser Adjustable Synthetic Epikeratoplasty," Refractive & Corneal Surgery, vol. 5, Jan./Feb. 1989, pp. 46–48.

Thompson, K., "Will the Excimer Laser Resolve the Unsolved Problems with Refractive Surgery?", Refractive & Corneal Surgery, vol. 6, Sep./Oct. 1990, pp. 315–317.

* cited by examiner

METHOD AND APPARATUS TO CORRECT REFRACTIVE ERRORS USING ADJUSTABLE CORNEAL ARCUATE SEGMENTS

1. RELATED APPLICATIONS

This patent application claims 119(e) benefit of prior Provisional Application No. 60/071,405, filed Jan. 14, 1998.

2. FIELD OF THE INVENTION

This invention relates to a method and apparatus for adjusting corneal curvature and, more particularly, to an implantable device adapted for insertion into the cornea of an eye which may be modified in the amount of volume it displaces at the time of insertion and at post-operative times to correct various refractive errors by adjusting or removing solid material from the implanted device or augmenting said device with solid material.

3. BACKGROUND OF THE INVENTION

Figure 1:
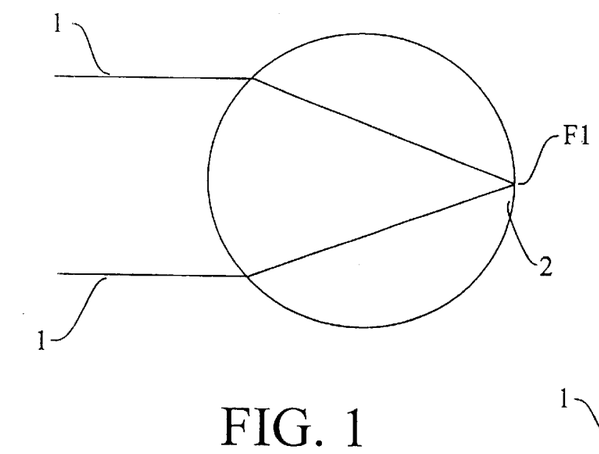
FIG. 1 is a schematic representation of a horizontal section of the human eye.
Figure 2:
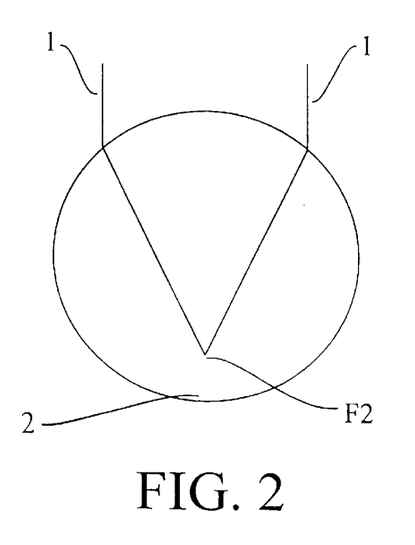
FIG. 2 is a schematic representation showing how the light rays focus in front of the retina of the eye in the condition of myopia.
Figure 3:
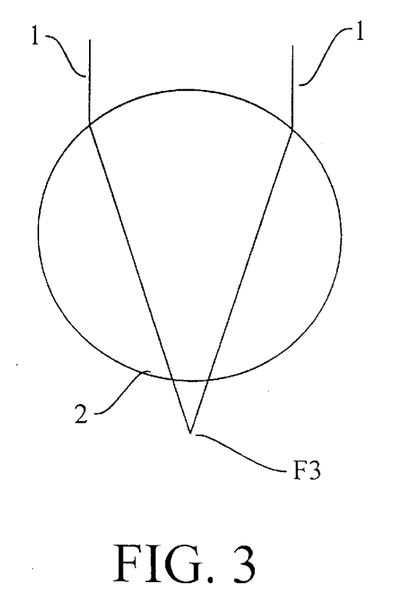
FIG. 3 is a schematic representation showing how light rays focus in front of the retina of the eye in the condition of myopia.

Ametropia, an undesirable refractive condition of the eye, has three main subdivisions; myopia, hyperopia, and astigmatism. FIG. 1 is a schematic representation of an eye which shows parallel light rays 1 focusing on the retina 2 at F1. In myopia, by far the most common type of ametropia, the parallel light rays 1 which enter the eye as shown in FIG. 2 come to a focus F2 in front of the retina 2 as shown in FIG. 2. In hyperopia, the rays of light 1 come to a focus F3 behind the retina 2 as shown in FIG. 3. When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye which acts to change the light-bending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomileusis which can steepen or flatten the central cornea. Keratomileusis was introduced by Barraquer of Columbia in 1961 and essentially involves grinding a corneal button into an appropriate shape to correct the refractive error and replacing the reshaped corneal button. Some of the more common keratorefractive procedures are discussed below, none of which have currently shown itself to have all the characteristics of an ideal keratorefractive procedure. The disadvantages of corneal refractive surgery include limited predictability, lack of reversibility, corneal destabilization, optical zone fibrosis, post-operative discomfort, and visual symptoms such as glare, halos, and starbursts.

The ideal keratorefractive procedure possesses the following characteristics: adjustability, predictability, good quality of vision (absence of post-operative glare and haloes), reversibility, stability over time, safety, and low cost. Any refractive procedure that attempts to achieve visual outcomes similar to that which can be provided by glasses must incorporate the ability to post-operatively adjust the refractive outcome since there will be variability in outcome from either the surgical procedure or the wound healing response. Photorefractive Keratectomy (PRK), a currently popular procedure, hopes to achieve adjustability with re-ablation. There is little doubt that PRK reduces the variability of the surgical procedure and thus improves predictability. However, the percentage of patients achieving an uncorrected visual acuity of 20/20 is still only 50–60%. "Enhancement" procedures are performed when the patient is undercorrected. But since the surgical variability is reduced and the variable wound healing responsible for the bulk of the variability of the refractive outcome, it becomes necessary to have an "enhancement" procedure that minimally causes a wound healing response. Unfortunately, the only "fine-tuning" procedure available with PRK is yet another PRK. The supposedly second "enhancement" PRK also involves removal of the corneal epithelium and ablation of the corneal stroma. In essence, the fine-tuning procedure is just as invasive as the ball-parking procedure and is no more predictable than the initial procedure. Rather, the enhancement procedure has the potential to invoke a greater wound-healing response since the corneal stroma has undergone previous insult. It can be seen that a refractive procedure that truly allows adjustability must minimally disturb the cornea and cause a minimal wound-healing response.

For years it has been thought that refractive surgery with intracorneal implants could be used in the correction of ametropia. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's (keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses include surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention.

In the Foreword to the textbook, Principles and Practice of Refractive Surgery, Jose Barraquer writes, "As a result of my initial publications, some authors decided to try different methods to modify the shape of the cornea. Punch stromectomy and temporal inclusion of a plastic disk by Krawawicz (1960), the use of a trephine by Pureskin (1967), soto impronta by Strampelli (1964), molding by Martinez and Katsin (1965), and corneal rings by Blawatkaia (1966) all were tried."

Zhivotosvskii, D. D., USSR Patent No. 3887846, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the ring are not described.

A. B. Reynolds (U.S. Pat. No. 4,452,235) describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia:

1. The first problem is concerned with the ability to predetermine the shape and size of a implant that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.
2. The refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area,—the inherent individual variability, in that while the outcome may be stable, it may very well be an inadequate refractive outcome that is stable.

Another unaddressed issue is that even with the implant, surgeons will aim for a slight under-correction of myopia because, in general, patients are more unhappy with an over-correction that results in hyperopia. Again, the refractive outcome may be more stable than in RK or PRK but it may be an insufficient refractive result that is stable.

Simon in U.S. Pat. No. 5,090,955 describes a surgical technique that allows for modification of the corneal curvature by inter-lamellar injection of a synthetic gel at the corneal periphery while sparing the optical zone. He does discuss removal of gel to decrease the volume displaced and thus adjust the final curvature of the central corneal region.

Siepser (U.S. Pat. No. 4,976,719) describes another ring-type device to either flatten or steepen the curvature of the cornea by using a retainer ring composed of a single surgical wire creating a ring of forces which are selectively adjustable to thereby permit selective change of the curvature of the cornea,—the adjustable means comprising a turnbuckle attached to the wire.

The mechanism by which corneal rings flatten the central corneal curvature is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called 'keratomileusis' and those involving addition received the name of 'keratophakia'. Intrastromal corneal rings add bulk to the periphery and increasing the thickness of the ring results in a more pronounced effect on flattening of the anterior corneal curvature by "increasing (thickness) in its periphery".

The ideal keratorefractive procedure allows all the advantages of eyeglasses or contact lenses, namely, being able to correct a wide range of refractive errors, accuracy or predictability, allowing reversibility in the event that the refractive state of the eye changes and it becomes necessary to adjust the correction again, yielding minimal complications, and associated with technical simplicity, low cost, and being aesthetically acceptable to the patient. The goal of refractive surgeons should be to achieve 20/20 uncorrected visual acuity with long-term stability in greater than 95% of patients. None of the currently available refractive surgery procedures generate this degree of accuracy or stability.

Once again, an easy procedure to post-operatively fine-tune the refractive correction and corneal curvature which is often influenced by changes in corneal hydration status, wound healing responses, and other unknown factors, is not available. Each of the techniques described suffers from a limited degree of precision either due to a variable surgical procedure, a variable wound healing response, or variability in both the surgical procedure and wound healing. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

4. SUMMARY OF THE INVENTION

The present invention concerns the use of adjustable corneal arcuate segments adapted for implantation in the cornea and formed of a flexible hollow shell composed of a natural or synthetic polymer material such as a silicon or urethane polymer, with an annular chamber that may be augmented with a biocompatible filler material such as polymethylmethacrylate (PMMA). The filler material can be any biocompatible material of any shape or length but preferably is a flexible elongated strand-like filament of a variable size. The arcuate segments are filled with a predetermined amount of the biocompatible material described, and implanted in the cornea in surrounding relation to the optical zone of the cornea. The corneal curvature is then adjusted by complete removal of one or more strands thus modifying the volume of the device in a discrete fashion and resulting in steepening of the corneal curvature. This relatively simple adjustment for refractive correction can be performed with surgical instruments commonly available and requires minimal post-operative manipulation of the cornea and the implanted arcuate segment. The apparatus of the invention is an adjustable implantable device including an outer membrane forming an enclosure for receiving a filler material such as multiple strands and adapted to be inserted into the interlamellar space of the corneal stroma for the purpose of correcting refractive error. The volume displaced by the device is easily modified on multiple occasions following the initial surgery of implantation and thus allows for adjustment of the refractive outcome at a later date without necessitating the removal of the implanted device.

5. BRIEF DESCRIPTION OF THE DRAWINGS

FIGS. 16(c–d) are radial cross-sectional views through line 16b of FIG. 16(a).

FIG. 17(a) is a plan view of a relatively shorter annular segment with a variable width.

FIGS. 17(b–c) are radial cross-sectional views through line 17a of FIG. 17(a).

FIGS. 17(d–e) are radial cross-sectional views through line 17b of FIG. 17(a).

FIGS. 18(a–b) are plan views of annular segments which are implanted off-axis to one another for the treatment of irregular astigmatism.

6. DETAILED DESCRIPTION OF THE INVENTION

The disclosure of the pending U.S. patent application Ser. No. 08/829,846 filed Apr. 1, 1997 and application Ser. No. 08/856,650 filed May 15, 1997 are incorporated herein by reference. The disclosure of the provisional application entitled "Method and apparatus for adjusting corneal curvature", filed Aug. 4, 1997 and describing sub-embodiments that "may have an arc length of approximately 160 degrees±15 degrees such that two halves of an annular device are implanted in the lamellar channel opposite to each other", is also included herein by reference.

Figure 4:
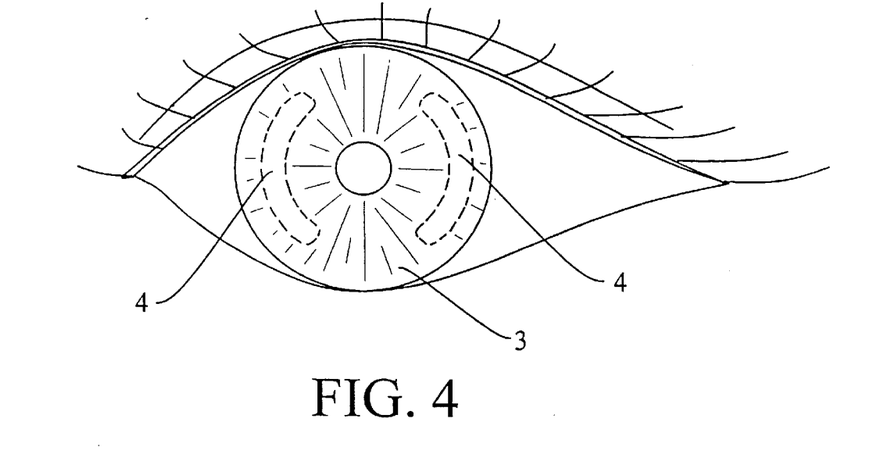
FIG. 4 is a schematic illustration showing an eye with adjustable annular corneal segments implanted within the cornea.

Referring more particularly to the drawings, there is shown in FIG. 4 the apparatus of the invention which is comprised of adjustable corneal annular segments 4 implanted within the cornea 3 of the eye. The adjustable corneal annular segment is formed of an enclosure as demonstrated in FIG. 5 for receiving a filler which is easily removable after the annular segment is implanted into the cornea. The filler material and outer shell have been described in detail in the previously referenced disclosures and includes various polymeric materials. The filler material is preferably a flexible, filamentous, strand-like structure. The cross section of the strands may be of various geometric shapes including circular, oval, rectangular, square, or triangular. The cross-sectional area of the strand can vary in dimension along its length. Each arcuate segment may contain one or more strands and each strand is removable at a later time. The arcuate segments are crescent-shaped when seen in a perspective view, as shown in FIG. 5.

Figure 5:
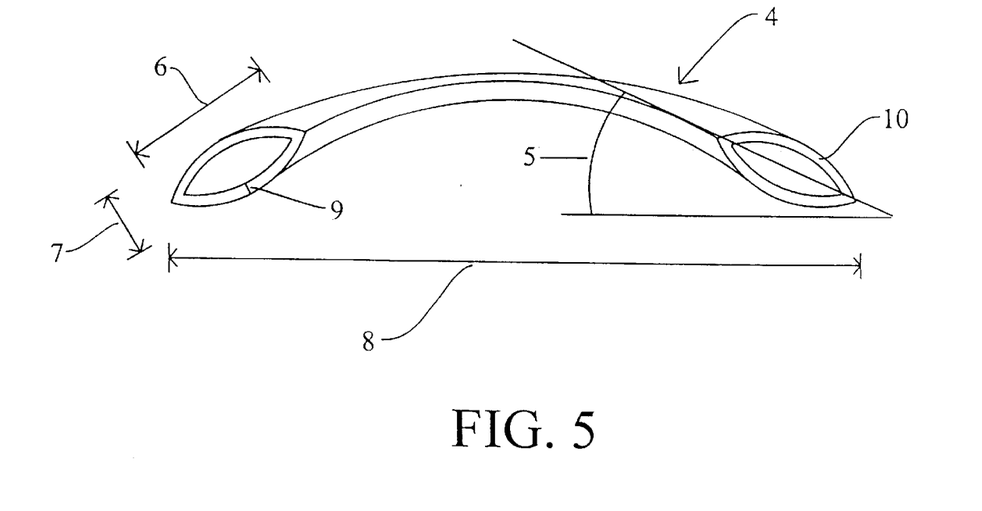
FIG. 5 is a perspective view of the shell of the annular corneal segment.
Figure 6:
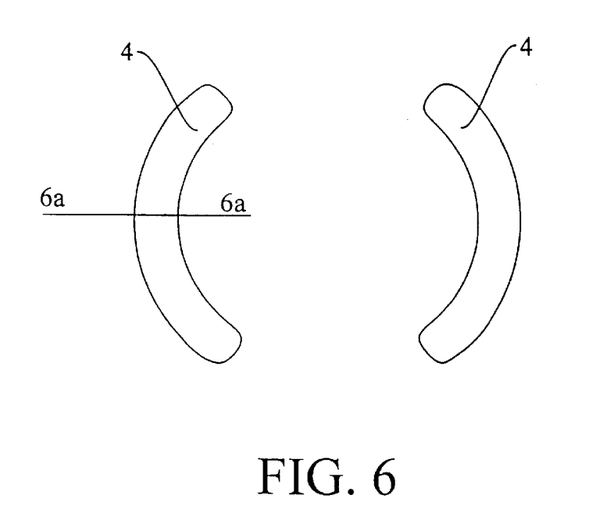
FIG. 6 is a plan view of the adjustable annular corneal segments.
Figure 7A:
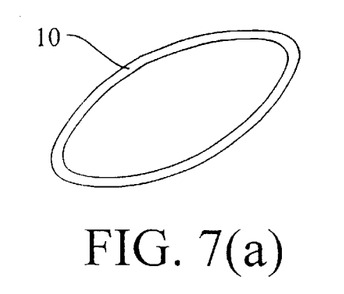
FIGS. 7(a)–(d) are radial cross-sectional views through line 6a of FIG. 6, of various geometric shapes that the shell of the annular corneal segment can form.
Figure 7B:
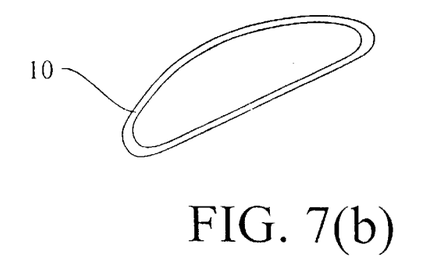
Figure 7C:
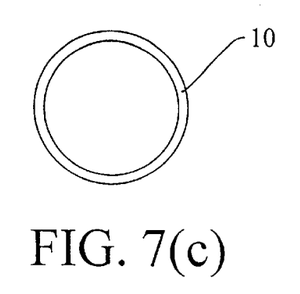
Figure 7D:
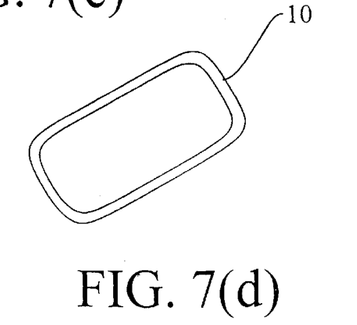

Referring to FIG. 5, the adjustable corneal annular segment comprises a tubular shell 10 made of a flexible material, such as a silicone, acrylic or urethane polymer. The outer shell of the annular segment can have a variable arc length. The outer shell material may extend over the ends of the annular segments such that the ends are closed to the surrounding tissue. In the correction of astigmatism, the annular segment may have an arc length of 80 degrees±40 degrees. In situations where more than one annular segment is placed into the cornea but there is no attempt to significantly correct astigmatism alone, the arc length is approximately 360 degrees divided by the number of segments to be implanted±30% of that arc length. For instance, when three segments are to be implanted, the arc length of each individual annular segment will be approximately 120 degrees±45 degrees. There may be up to four annular segments. The arc length of the segments in the correction of myopic astigmatism is further described later.

Figures 8A, 8B:
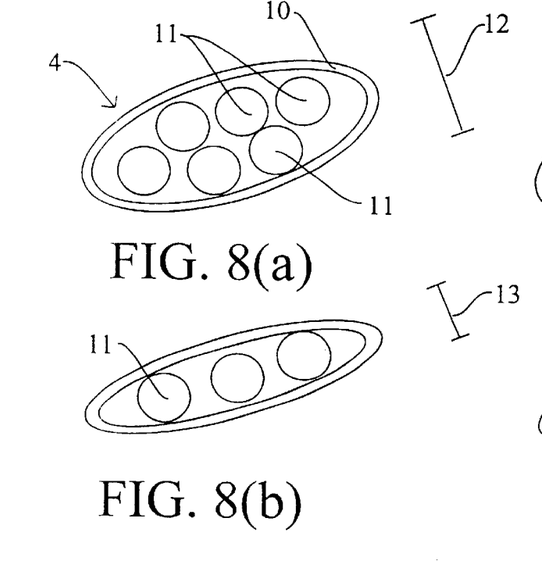
FIG. 8(a) is a radial cross-sectional view of the annular segment filled with strands.
FIG. 8(b) is the view of FIG. 8(a) after strands have been removed, demonstrating shell collapse.

The shell material has adequate stiffness such that the device will maintain its generally circular shape in plan view hen sufficiently filled and also have adequate flexibility to allow an increase in thickness with filling as shown in the cross section view of FIG. 8(a) and flattening with removal of the ring as shown in FIG. 8(b). The shell of the device must have sufficient structural integrity, strength and flexibility to generally maintain its shape and be expandable. Its composition material may be similar to that used in producing foldable or deformable intraocular lenses such as a silicone polymer, urethane polymer or acrylic polymer, or that material used in soft contact lenses or materials such as fluoropolymer resins or polyesters. Examples of other medical devices composed of materials which may be suitable for the shell of this invention or the filler material of this invention include vascular graft tubing, dialysis tubing or membrane, blood oxygenator tubing or membrane, ultrafiltration membrane, intra-aortic balloon, catheter, and suture. The shell or the filler material may be composed of one or more natural or synthetic polymers.

The dimensions as shown in FIG. 5 include a thickness 7 of 0.1–1.5 mm, width 6 of 0.4 to 2.0 mm and a radius of curvature similar to a ring of outer diameter 8 of 4.00 to 11.0 mm. The thickness of the shell 10 of this device 4 may be varied. The major axis of a transverse cross section of the device is such that it corresponds to the slope of the corneal arc of the anterior pole of the cornea, thus forming the conic section. This angle 5 is approximately 25 to 35 degrees as shown in FIG. 5. The cross section of the adjustable corneal annular segment as taken in a radial plane is typically elliptically shaped but can have a radial cross-section of various geometric shapes as seen in the section views demonstrated in FIGS. 7(a)–7(d). The different embodiments can each be modified to provide a number of sub-embodiments by altering variables such as the composition material of the device wall, type of filler material, and cross-sectional surface parameters of the device, e.g., forming the device from cross sections in the form of a circle, square, rectangle, triangle, oval, etc.

The adjustable annular segments are adapted to be implanted into the peripheral stromal cornea. The segments are of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea intrastromally and consists of a flexible material which is biocompatible, and more specifically, compatible with ocular tissues.

Figures 9A, 9B:
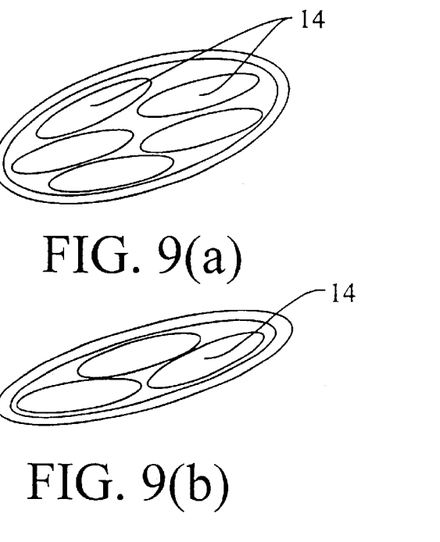
FIGS. 9–11 are views similar to FIG. 8 with the exception that the strands have varying radial cross-sectional shapes.
Figures 10A, 10B:
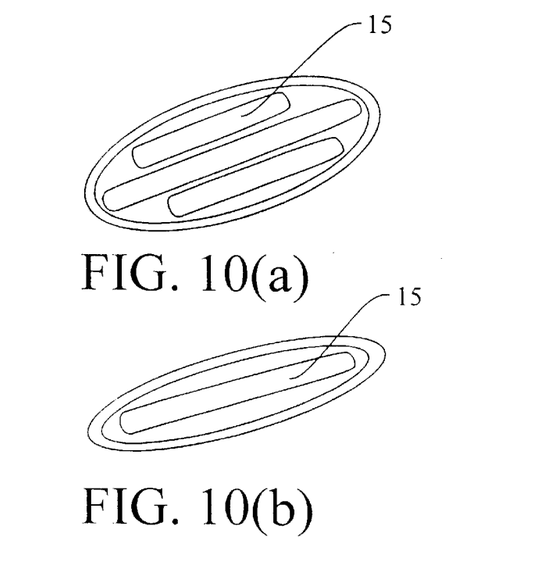
Figures 11A, 11B:
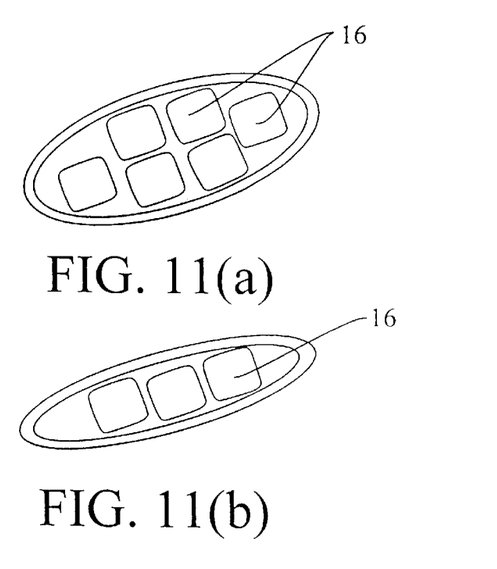
Figure 12:
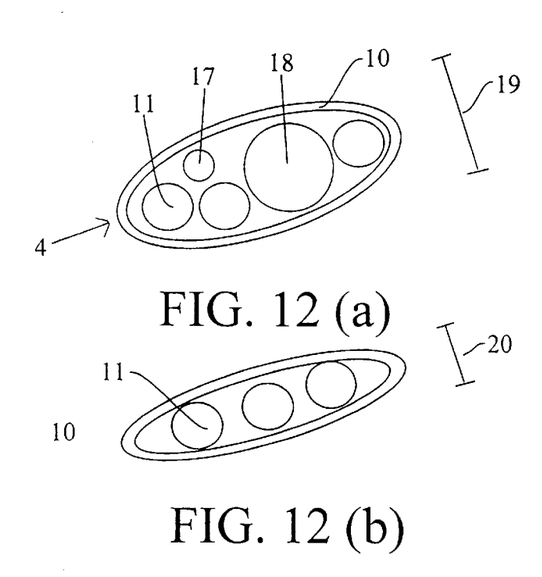
FIGS. 12–13 are radial cross-sectional views of the annular segment demonstrating strands with varying size and shape within the same annular segment.
Figures 13A, 13B:
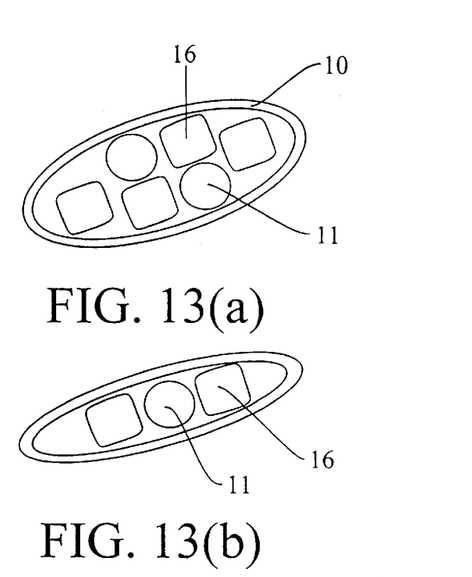

Referring to FIGS. 8–10, the arcuate-shaped segments may contain only one or multiple strands 11 of varying radial cross-sectional shape (11,14,15,16) diameter, and composition. The strands 11,14,15,16 may be composed of a permanent biocompatible material as used in ophthalmic surgery such as polymethylmethacrylate, nylon, mersilene, prolene, or polypropylene and can vary from 0.02 mm in diameter to 1.0 mm in diameter. The strands may be clear or colored. The strand may be marked to aid the surgeon in differentiating between different size strands. FIG. 8(a) demonstrates a radial cross-section of an annular segment 4 with an outer shell 10 containing biocompatible material such as strands 11. FIG. 8(b) shows the annular segment of FIG. 8(a) after a few strands have been removed from the outer shell. It can be seen that the annular segment of FIG. 8(b) has a small radial cross-sectional area and is also thinner than the annular segment of FIG. 8(a). FIGS. 9–13 also demonstrate annular segments with various shape strands within the outer shell before and after strand removal. The strands can have radial cross-sectional shapes such as an oval 14, rectangular 15, or square 16. As shown in FIGS. 12,13, the outer shell may contain strands that vary in radial cross-sectional size or shape.

Figure 14A:
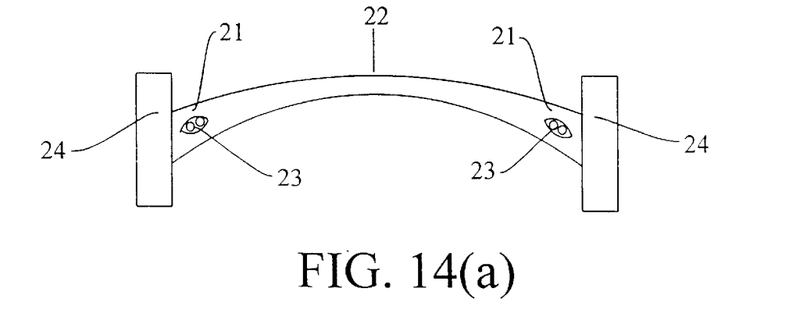
FIG. 14(a) is a schematic representation of the cornea with adjustable annular segments implanted within the peripheral cornea.
Figure 14B:
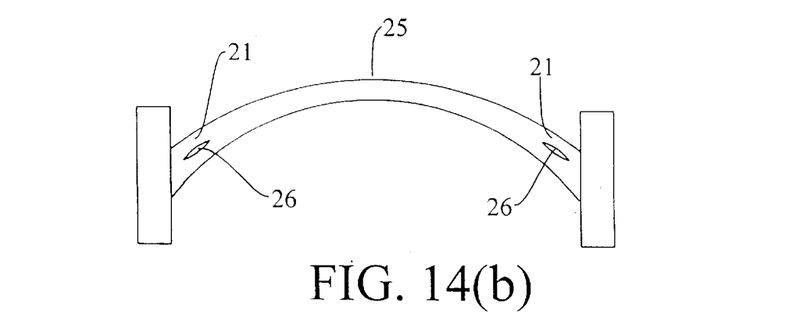
FIG. 14(b) is the view of FIG. 14(a) demonstrating that the corneal curvature steepens when strands are removed from the implanted annular segments.

FIG. 14 is a schematic representation of the adjustable annular segments within the peripheral cornea 21 before and after strand removal from the annular segments. The cornea 21 is supported on each end by the limbus which is represented by poles 24. FIG. 14(a) shows the annular segments 23 with the strands in place. The curvature 22 is relatively flat. FIG. 14(b) shows that the corneal curvature 25 has increased following strand removal from the implanted annular segments 26.

The adjustable annular segments may have several different mechanisms of adjustment. Adjusting the radial cross-sectional area of the segment after implantation by removing biocompatible material from the outer shell of the segment has been described. Adjusting the radial cross-sectional area of the segment can also be achieved as described for a fluid-filled adjustable corneal ring, U.S. patent application Ser. No. 08/856,650 which has been included herein by reference. Adjusting the radial cross-sectional area of the implanted segment can also be achieved using the mechanism described in this author's provisional patent, entitled "Method and Apparatus for Adjusting Corneal Curvature using Laser Energy", filed Aug. 4, 1997, which is also included herein by reference. This particular mechanism involves using the laser to heat-shrink material within the outer shell causing a decrease in radial cross-sectional area of the implanted segment.

Depending on the amount of refractive error, an appropriate arcuate segment embodiment varied in radial cross-sectional shape, size, strand size, strand composition number of strands, and strand length are chosen. The more peripherally in the cornea the arcuate segment is placed, the less the refractive effect. Adjustable arcuate segments placed closer to the central cornea can potentially correct up to 20 diopters of myopia. Arcuate segments placed at a lesser depth within the corneal stroma are also expected to have a greater refractive effect. The size of the adjustable corneal arcuate segments chosen should be such that the range of over-correction or under-correction secondary to individual variability of response to surgery may be comfortably corrected (not requiring removal of all of the strands) by the methods described. The ideal embodiment, given the pre-operative refractive state and other pertinent data, is chosen prior to operating and then that embodiment further manipulated at a later time as necessary to determine the ideal curvature.

The adjustable annular segments are implanted into an annular lamellar channel formed at approximately ½ to ⅔ corneal depth. However, as mentioned, segments implanted at a lesser depth (⅓ to ½ corneal depth) may have a greater refractive effect. A small radial incision is made at a pre-determined corneal radius. A lamellar channeling tool is then introduced through the incision and rotated to produce an annular channel at the pre-determined radius at around ⅔ corneal depth. The channeling tool is then removed. The adjustable annular segments are then implanted into the annular lamellar channels. The segments may be inserted into position within the lamellar channels. The shorter segments insert into the channels more easily. Longer segments may need to be pulled into place using a circular hooked instrument. If the circular hooked instrument is used, the hook is attached to a loop pre-formed on the leading end of the segment and the circular hooked instrument rotated until the segment is progressively pulled into place. If a continuous 360 degree lamellar channel is present, the circular hooked instrument may be used from either direction; if the instrument is inserted in the opposite direction, it is used to pull the segment into place and if the instrument is inserted in the same direction, it is used to push the leading end of the segment forward. If a shorter arcuate channel is present, it is apparent that the instrument will not be able to be inserted from the opposite direction and still attach to the leading end of the segment. More than one radial incision may need to be placed if shorter arcuate channels are formed which are not continuous. Post-operative adjustments are made by removing strands from the implanted adjustable corneal arcuate segments. The adjustments are made using principles described in pending disclosures.

Referring to FIGS. 15–18, the adjustable corneal arcuate segments may also be used to correct astigmatism. Curvature variation of the anterior surface of the cornea is responsible for the majority of cases of astigmatism. The light rays converge upon more than one plane and no one principal focus is formed. Astigmatism ordinarily depends on the presence of toroidal instead of spherical curvatures of the refractory surfaces of the eye. It thus becomes obvious that to correct astigmatism certain areas of the cornea must necessarily be corrected to a greater degree than other areas. The arcuate segments can be implanted in the areas of the cornea having a steeper slope and requiring greater correction.

If correction is attempted for myopia alone, the adjustable corneal arcuate segments can also be implanted intrastromally in a pattern as shown in FIGS. 15(*a,c,e*). Typical adjustable arcuate segments for the correction of myopia alone subtend 27 approximately 150 degrees±30 degrees. In general, if induced astigmatism is to be avoided, the ends of the arcuate segments will be implanted relatively close to one another. The radius of curvature can be similar to a ring of outer diameter 8 of 4.00 to 11.0 mm. As previously described, in situations where more than one annular segment is placed into the cornea but there is no attempt to significantly correct astigmatism alone, the arc length is approximately 360 degrees divided by the number of segments to be implanted±30% of that arc length. For instance, when three segments 31 are to be implanted, the arc length of each individual annular segment will be approximately 120 degrees±45 degrees. There may be up to four annular segments 35. The arcuate segments are not necessarily the same length in a particular patient. For example, one segment from FIG. 15(*a*) may be combined with two segments 35 from FIG. 15(*e*). The arc length of the segments in the correction of myopic astigmatism is further described later.

As demonstrated in FIG. 15(*b,d,f*), If correction is attempted for myopic astigmatism, the adjustable corneal arcuate segments can also be implanted intrastromally. Typical adjustable arcuate segments for the correction of myopic astigmatism can range from 80 degrees±40 degrees up to 150 degrees±40 degrees. Arcuate segments with dimensions falling within the first range (80±40 degrees) are more likely to be beneficial for mild hyperopic astigmatism with a spherical equivalent of zero, astigmatism without myopia, or low levels of myopia with various amounts of astigmatism. These arcuate segments falling within the first range are further described in conjunction with FIGS. 16–18. The arcuate segments having the larger dimensions (150 degrees±40 degrees), for the correction of myopic astigmatism will be further described below.

Figure 15A:
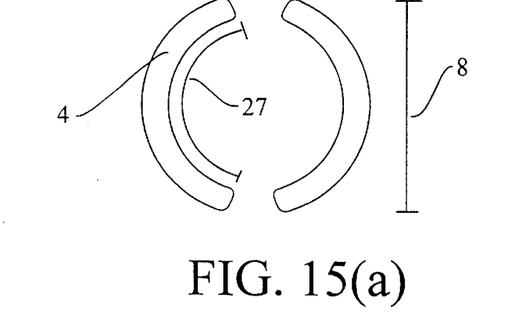
FIG. 15 are various plan views of the annular segments showing multiple segments and segments that have a variable width.
Figure 15B:
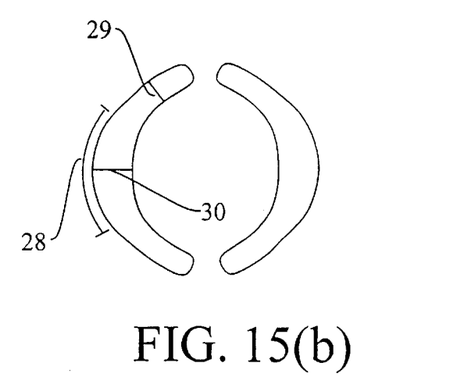
Figure 15C:
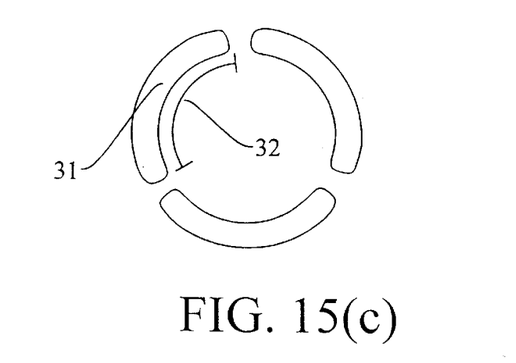
Figure 15D:
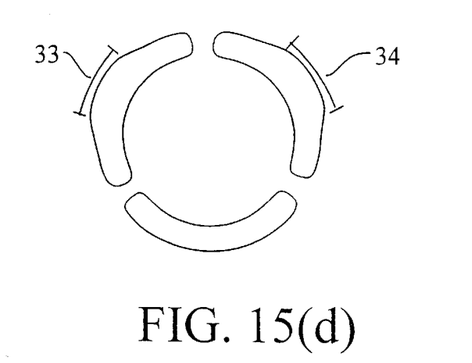
Figure 15E:
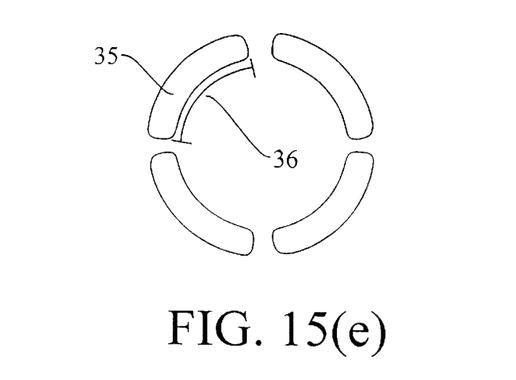
Figure 15F:
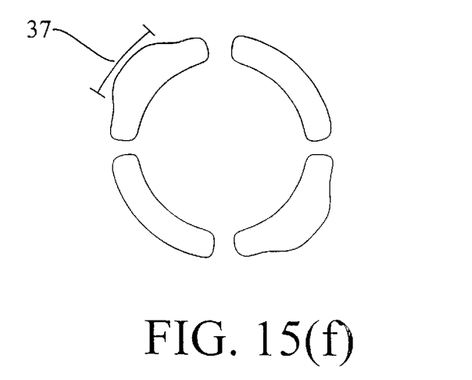

In myopic astigmatism, all areas of the mid-peripheral cornea have areas of steepness with some areas having a relatively steeper slope requiring greater correction. The greater correction is achieved by varying the radial cross-sectional area on the adjustable arcuate segments. The adjustable arcuate segments are implanted such that the segment areas 28,33,34,37 having the larger radial cross-sectional areas correspond to the corneal areas requiring greater correction. The total arc length for the adjustable arcuate segment of 150 degrees±30 degrees. The areas having the larger radial cross-sectional area have an arc length of ¼ to ¾ the arc length of the particular segment. There may be unique situations when the arcuate segment must be specially made with dimensions falling outside these ranges. As described in the U.S. patent Ser. No. 08/829,846, the radial cross-sectional area can be increased relative to other areas on the arcuate segment by increasing the thickness of the shell or increasing the number of size of strands within the shell. Again, the arcuate segments are not necessarily the same arc length in a given patient. For example, a segment from FIG. 15(*b*) may be combined with two segments from FIG. 15(*f*).

Figure 16A:
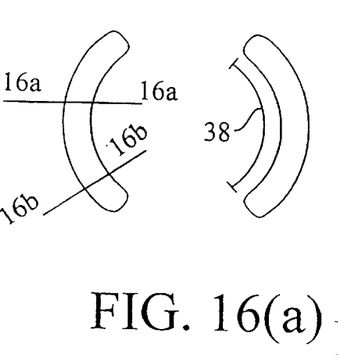
FIG. 16(a) is a plan view of a relatively shorter annular segment.
Figure 16B:
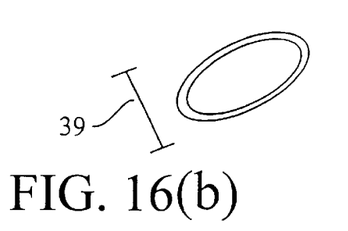
FIG. 16(b) is a radial cross-sectional view through line 16a of FIG. 16(a).
Figures 16C, 16D:
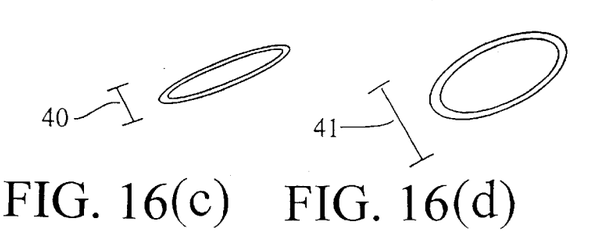
Figures 17A, 17B, 17C, 17D, 17E:
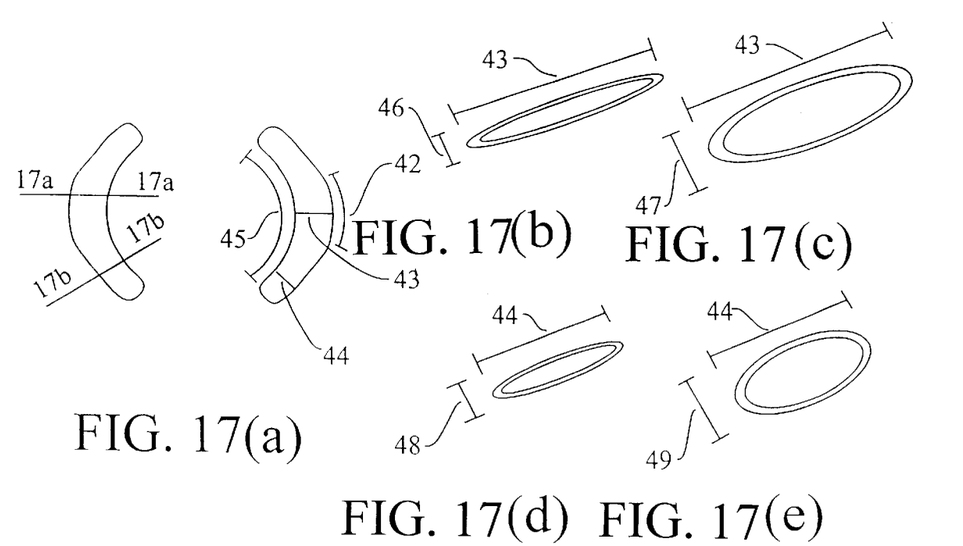
Figure 18:
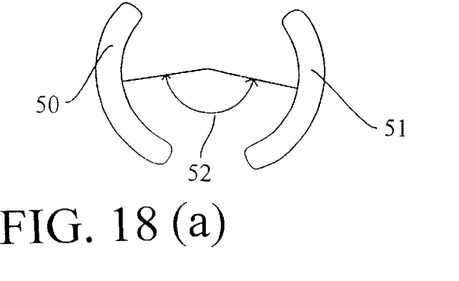
Figure 19A:
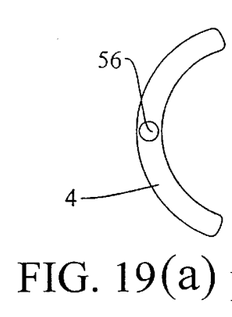
FIG. 19 are plan views of an annular segment with openings in the anterior shell of the annular segment having various geometric shapes, various positions, and various combinations.
Figure 19B:
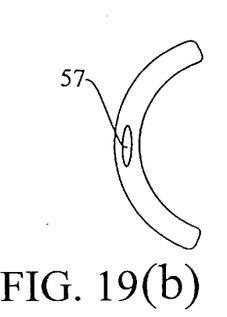
Figure 19C:
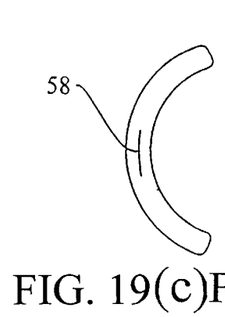
Figure 19D:
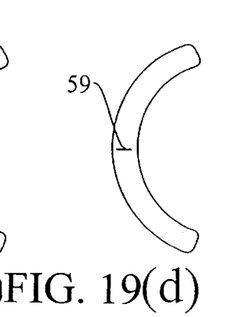
Figure 19E:
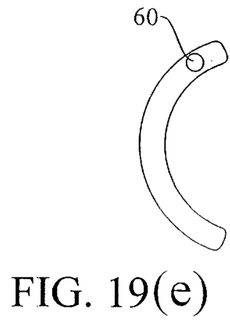
Figure 19F:
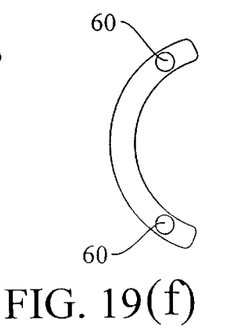
Figure 19G:
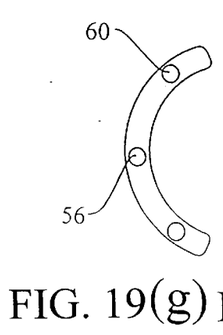
Figure 19H:
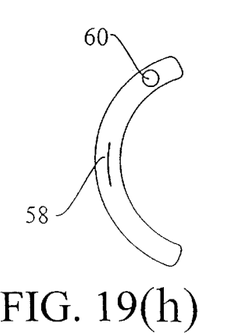

As demonstrated in FIGS. 16–18, if correction is attempted for astigmatism alone, then short adjustable arcuate segments are implanted intrastromally within arcuate channels. The adjustable arcuate segments are implanted in the areas of the cornea having a relatively steeper slope. The arcuate segment length and radial cross-sectional area are pre-determined to adequately correct the individual's particular amount of astigmatism. As seen in FIG. 16(*a*), typical arcuate segments for the correction of astigmatism alone subtend 38 approximately 80 degrees±40 degrees. A particular size segment will have a given effect at correcting astigmatism at a given corneal radius; decreasing the corneal radius at which the same arcuate segment is implanted will increase the effect of that particular segment. The annular segments may correct astigmatism by having a relatively short arc length alone or by varying the thickness of the annular segment as shown in FIGS. 16(*b–d*). The thickness of the annular segment 39, 40 or 41 can be varied such that the segment is thinner towards the ends. The annular segments may correct astigmatism by varying the width of the annular segment as shown in FIG. 17. The arc length 45 of the annular segments has been described. The arc length of the wider portion 42 can be ¼ to ¾ the arc length of the segment. The width 43 of the wider portion can be up to twice the width of the narrower portion 44. The thickness can be varied also 46,47,48,49.

Typically, the astigmatism will be regular and the steeper areas of cornea located 180 degrees away from each other. In these circumstances, the arcuate segments will also be implanted 180 degrees away from each at the steep areas. However, there will be instances of irregular astigmatism and the steeper areas may not be exactly 180 degrees away from each other. Also, in the situation of irregular astigmatism, the amount of steepness in the areas may not be identical. Using topographic data, it may be desirable to implant different thickness arcuate segments in the various steep corneal regions with the thicker segments corresponding to the steeper areas. In these situations, best detected by corneal topography, the arcuate segments will not be placed symmetrically around the optical axis, but reflect the irregular astigmatism as demonstrated in FIG. 18. Short arcuate segments 50,51 with a consistent width may be implanted in an off-axis fashion. Segments 53,54 with a variable width or thickness may also be implanted in an off-axis fashion to correct irregular astigmatism.

Figure 20:
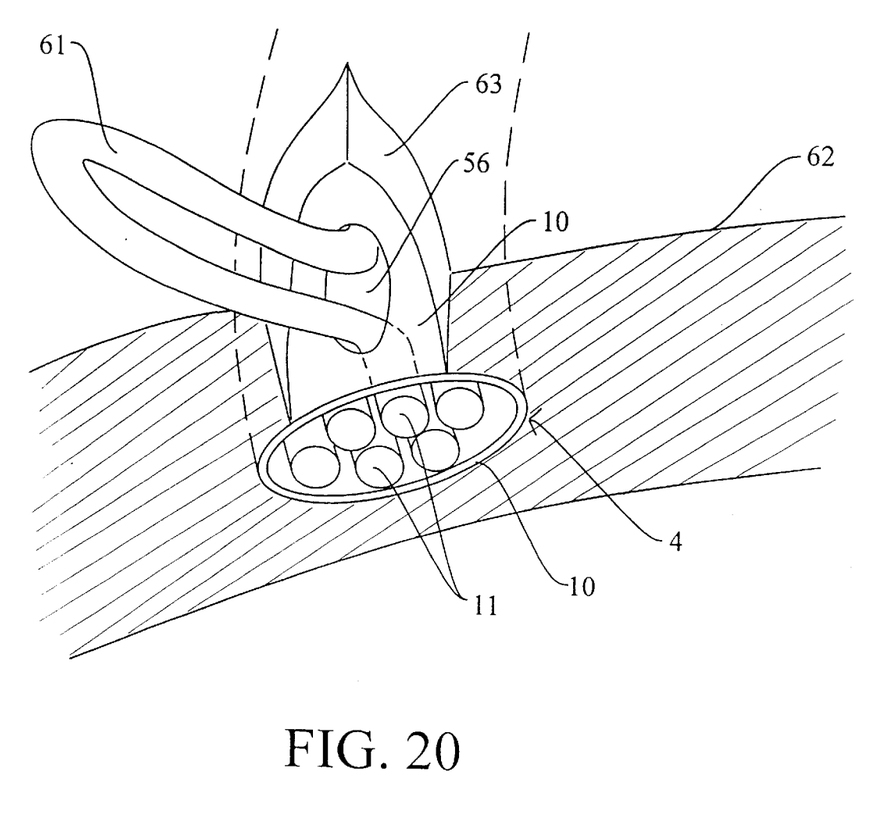
FIG. 20 is a perspective view of an annular segment with an opening in the anterior shell which is implanted in the cornea; the cornea has an incision made anterior to the opening of the shell and the removal of a strand from the implanted annular segment is demonstrated.

If there is overcorrection of the astigmatism after implantation of the adjustable arcuate segments, filler material or strands from the arcuate segments may be removed from the arcuate shell. There may or may not be an opening placed in the anterior shell of the arcuate segment. Referring to FIG. 19, it can be seen that the opening in the anterior shell of the arcuate segment may have various geometric shapes such as circular 56, oval 57, a concentric slit incision 58, or a radial slit incision 59. There may be more than one opening 60, the placement of the opening along the anterior shell of the arc segment may vary, and various combinations of the different geometric shapes may be present. As seen in FIG. 20, if there is an opening placed 56, the corneal incision 63 is made anterior to the opening for the removal of strands. This incision is made into the anterior corneal stroma at a point anterior to the shell 10 of the arcuate segment and an iris hook or other similar instrument used to remove one or more strands 11 as necessary to adjust for the overcorrection. A loop of strand 61 is shown in the process of removal. If no opening is present, when the incision is made anterior to the segment, it can be made sufficiently deep to cut the anterior shell of the arcuate segment. Implanted arcuate segment adjustment is also based on adjustment principles described in previous disclosures by the inventor.

In yet another useful embodiment, the outer shell of the implantable device is composed of a biocompatible, porous polymer material such as a microporous polypropylene tube. The characteristics of the porous shell are similar to that already described including sufficient flexibility to allow the thickness of the device to decrease when the biocompatible filler material is removed. Advantages of a porous shell include improved nutrient diffusion to the anterior corneal stroma.

Another method to allow improved nutrient diffusion to the anterior cornea stroma is to place openings in the shell of the implant. The openings may be multiple, radially or longitudinally oriented, of variable length and with and situated on the anterior or posterior surface of the device.

It is therefore to be appreciated that by use of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well-suited to adjust a hyperopic refractive outcome. 2) Irreversibility of radial keratotomy and laser ablation surgeries. 3) Surgical manipulation of the central visual axis with the potential for scar and stromal haze formation following laser ablation procedures. 4) The need for chronic use of steroid drops with its accompanying complications such as cataract and glaucoma. 5) Regression with laser ablation procedures, especially following re-operation. 6) Reduction of positive sphericity with RK and laser ablation which may result in increased image aberration. 7) The invasiveness of laser in-situ keratomileusis. 8) Lack of precision and predictability with all current procedures. 9) The possible need for repetitive explanting and implanting of ICR'S, which may cause shearing of corneal peripheral channel lamellae with associated decrease in effect and also scar formation.

The last point requires further elaboration. Methods to adjust ring thickness have been described in the prior art. These methods are only discussed in relation to adjusting the ring thickness during implantation, not post-operatively. Attempts to adjust the thickness of the ring are most useful after corneal curvature has essentially stabilized. Adjustments of devices that have been described in the prior art would necessarily require rotation of the ring with resultant shearing of the corneal-ring interface. Rotation of the ring would be required to allow more or less overlap of the individual ring parts thus increasing or decreasing ring thickness. This shearing of the corneal tissue in the immediate vicinity of the ring may alter the corneal curvature in an unpredictable fashion and probably also cause more scarring with possible unpredictable long-term effects. In the embodiment that is described in this article, the device volume is adjusted with only very minimal disturbance of the surrounding tissue. By the nature of the adjustment, there is no rotational movement of the aspect of the device which is in contact with the corneal tissue with respect to the cornea. The corneal-device interface is essentially undisturbed. Of course, with a decrease in the volume of the device, there will be a minute shift of surrounding tissue. In conclusion, a slight decrease in device volume by the adjustment described will not only be much easier to perform, but also have a much more predictable effect.

Dr. R. Eiferman in the Journal of Refractive and Corneal Surgery states that "if we can regulate the amount of tissue that is either added to or subtracted from the cornea and control the biological response, we may then be able to optimize refractive surgery". The ideal method to control the biological response is to minimally disturb corneal tissue, thus minimally inciting a wound healing response.

Dr. K. Thompson, in the same Journal asks "will it be possible for a refractive surgery technique to bypass the variable effects of corneal wound healing altogether?" That is unlikely for any initial keratorefractive procedure but the adjustable corneal annular segments of the present invention makes possible an adjustment that avoids the variable effects of corneal wound healing by minimally disturbing corneal tissue Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. This new espoused device allows for the fact that individual tissue response to the calculated correction may not be completely predictable, and permits easy adjustments at the time of surgery and more importantly, at a later date after corneal hydration and would healing responses have stabilized by simple ring removal from the device or replacement. The nature of these adjustments minimally disturb the implant-corneal interface (unlike the explantation of the ICR) and is thus expected to have a much more predictable effect than even the implantation of the device itself which causes less of a wound healing response than current procedures such as RK and PRK. In addition, when correcting myopia, a hyperopic outcome is very difficult to correct with any of the current kerato-refractive procedures and over-correction of myopia does occur. In this invention, a hyperopic outcome is relatively easily reversed by ring removal from the implanted device. Typically, in most kerato-refractive procedures for myopia, the surgeon aims for a slight under-correction because of the wish to avoid a hyperopic outcome. The ease with which a hyperopic outcome is adjusted with the device of the present invention enables the surgeon to aim for full correction, thereby obtaining the full benefit of the nomogram, and resulting in a higher percentage of patients with the desired refractive outcome even without a modification of the device. The surgeon may even choose to slightly overcorrect followed by a modification.

The essence of this invention lies in the assumption that individual responses to any kerato-refractive surgical procedures are variable, that even a "perfect" nomogram will not lead to a reliably predictable result in a particular individual, that a simple, safe, and effective technique for corneal curvature adjustment is necessary and that this modification should minimally disturb surrounding tissue thus allowing for a predictable effect. It should also be easily accomplished at some post-operative date after implantation of the device and after factors affecting corneal curvature changes have stabilized. A key feature of this invention lies in the ability of the device in its various embodiments to have its volume modified with ease at the time of implantation but more importantly on multiple occasions thereafter by simple removal of material from the implanted device, thus allowing fine-tuning of the refractive outcome.

In conclusion, in correcting refractive errors with this technique, the feeling of finality does not set in even with an initial inaccurate correction, with inadequate adjustment, or even when the last ring is removed because the device itself can be easily removed or better yet, left in place while other refractive procedures, such as laser ablation surgery are considered, if that point is ever reached.

It is also to be appreciated that the foregoing description of the invention has been presented for purposes of illustrations and explanation and is not intended to limit the invention to the precise form of apparatus and manner of practice herein. It is to be appreciated therefore, that changes may be made by those skilled in the art without departing from the spirit of the invention.

What is claimed is:

1. An adjustable intracorneal implant for placement into a human cornea for refractive correction comprising:
    a hollow, collapsible member that is crescent-shaped, the hollow member comprising a biocompatible material and having a cavity; and
    a solid filler material within the cavity of the hollow member that is removable after implantation of the corneal implant within the cornea.

2. The corneal implant of claim 1 wherein the solid filler material is comprised of a removable flexible strand within the cavity of the hollow member.

3. The corneal implant of claim 2 further comprising at least one additional removable strand.

4. The corneal implant of claim 2 wherein the perimeter of a cross-sectional area of the strand is angular.

5. The corneal implant of claim 2 wherein the perimeter of a cross-sectional area of the strand is curved.

6. The corneal implant of claim 1 wherein the hollow member comprises a flexible material.

7. The corneal implant of claim 6 wherein a radial cross-sectional area defined by the hollow member decreases following removal of at least one strand from the corneal implant.

8. The corneal implant of claim 1 wherein the radial cross-sectional area of the implant is largely comprised of a plurality of strands within the collapsible member.

9. The corneal implant of claim 1 wherein the radial cross-sectional area of the implant is largely comprised of the thickness of a wall of the collapsible member.

10. The corneal implant of claim 1 where the implant comprises an arc angle of about 120 to 180 degrees.

11. The corneal implant of claim 1 where the implant comprises an arc angle of about 60 to 120 degrees.

12. The corneal implant of claim 1 where the implant comprises an arc angle of about 30 to 60 degrees.

13. The corneal implant of claim 1 comprising one or more physiologically acceptable polymers.

14. The corneal implant of claim 13 wherein the solid filler material comprises a material selected form the group consisting of polymethmethacrylate, nylon, polyester, polypropylene, polyethylene, polysulfone, TEFLON, or interpolymers.

15. The corneal implant of claim 1 wherein the radial cross section of the implant has at least one area of comparatively larger dimension than other radial cross sections of the implant and are positioned to substantially correct astigmatism.

16. The corneal implant of claim 15 wherein the comparatively larger radial cross sectional dimension of the implant is largely due to the larger dimension of the solid filler material.

17. The corneal implant of claim 15 wherein the comparatively larger radial cross sectional dimension of the implant is largely due to the larger dimension of the walls of the collapsible member.

18. A process for altering the corneal curvature of an eye, the process comprising the steps of:
    making an incision into the cornea;
    at the incision, forming at least one crescent shaped channel between lamellae of the corneal tissue, said channel extending about an optical zone of the cornea; and
    implanting into the channel a corneal implant comprising a hollow, collapsible member that is crescent-shaped, has a cavity and which contains solid filler material within the cavity of the hollow member that is removable after implantation of the corneal implant within the cornea.

19. The process of claim 18 wherein the solid filler material comprises at least one strand of material extending along at least a portion of the corneal implant.

20. The process of claim 18 wherein if it is necessary to further alter the corneal curvature after the placement of the implant, the corneal curvature is altered by a process comprising;
    Making an incision into the anterior cornea at a point near the implant; and
    Removing solid filler material from the implant that is within the cornea.

21. The process of claim 20 further comprising the step of altering a radial cross-sectional area of the corneal implant.

22. The process of claim 20 further comprising the step of decreasing a radial cross-sectional area of the corneal implant.

* * * * *